United States Patent
Knauf et al.

(10) Patent No.: US 10,023,524 B2
(45) Date of Patent: Jul. 17, 2018

(54) PROCESS FOR PRODUCING NITROBENZENE

(71) Applicant: Covestro Deutschland AG, Leverkusen (DE)

(72) Inventors: Thomas Knauf, Dormagen (DE); Peter Drinda, Krefeld (DE)

(*) Notice: Subject to any disclaimer, the term of this patent is extended or adjusted under 35 U.S.C. 154(b) by 0 days.

(21) Appl. No.: 15/320,804

(22) PCT Filed: Jun. 22, 2015

(86) PCT No.: PCT/EP2015/063924
§ 371 (c)(1),
(2) Date: Dec. 21, 2016

(87) PCT Pub. No.: WO2015/197521
PCT Pub. Date: Dec. 30, 2015

(65) Prior Publication Data
US 2017/0174612 A1 Jun. 22, 2017

(30) Foreign Application Priority Data
Jun. 24, 2014 (EP) .................................. 14173583

(51) Int. Cl.
C07C 201/08 (2006.01)
C07C 201/16 (2006.01)
B01J 19/24 (2006.01)

(52) U.S. Cl.
CPC .............. *C07C 201/08* (2013.01); *B01J 19/24* (2013.01); *B01J 19/2465* (2013.01); *C07C 201/16* (2013.01); *B01J 2219/00006* (2013.01)

(58) Field of Classification Search
CPC .... C07C 201/08; C07C 205/06; C07C 201/06
See application file for complete search history.

(56) References Cited

U.S. PATENT DOCUMENTS

| 2,256,999 | A |   | 9/1941 | Castner |
| 2,739,174 | A |   | 3/1956 | Ross |
| 3,431,312 | A | * | 3/1969 | Bergmann .............. C07B 43/02 422/163 |
| 3,780,116 | A |   | 12/1973 | Sahgal |
| 4,772,757 | A |   | 9/1988 | Lailach et al. |
| 5,334,781 | A |   | 8/1994 | Kouwenhoven et al. |
| 5,763,697 | A |   | 6/1998 | Hermann et al. |
| 6,288,289 | B1 |   | 9/2001 | Boyd et al. |
| 6,562,247 | B2 |   | 5/2003 | Gillis et al. |

(Continued)

FOREIGN PATENT DOCUMENTS

| CN | 103080012 A | 5/2013 |
| EP | 0018247 B1 | 11/1985 |

(Continued)

*Primary Examiner* — Jafar Parsa
(74) *Attorney, Agent, or Firm* — N. Denise Brown

(57) ABSTRACT

The present invention relates to a process for the continuous production of nitrobenzene by the nitration of benzene with nitric acid and sulphuric acid under adiabatic conditions, not the entire production plant being shut down during a production stop, but the production plant being entirely or at least partly operated in recirculation mode. The invention further relates to a plant for producing nitrobenzene and to a method for operating a plant for producing nitrobenzene.

6 Claims, 2 Drawing Sheets

(56) References Cited

U.S. PATENT DOCUMENTS

| | | | |
|---|---|---|---|
| 7,326,816 B2 * | 2/2008 | Knauf | C07C 201/08 |
| | | | 204/450 |
| 7,344,650 B2 | 3/2008 | Knauf et al. | |
| 7,781,624 B2 | 8/2010 | Rausch et al. | |
| 8,357,827 B2 | 1/2013 | Munnig et al. | |
| 9,139,508 B2 | 9/2015 | Pennemann et al. | |
| 9,260,377 B2 * | 2/2016 | Knauf | C07C 201/08 |

FOREIGN PATENT DOCUMENTS

| | | | |
|---|---|---|---|
| EP | 04364433 | B1 | 4/1996 |
| WO | 2008148608 | A1 | 12/2008 |
| WO | 2011021057 | A1 | 2/2011 |

* cited by examiner

PROCESS FOR PRODUCING NITROBENZENE

CROSS-REFERENCE TO RELATED APPLICATIONS

This Application is a national stage application under 35 U.S.C. § 371 of PCT/EP2015/063924, filed Jun. 22, 2015, which claims the benefit of European Application No. 14173583.7, filed Jun. 24, 2014, both of which are incorporated by reference herein.

FIELD

The present invention relates to a process for continuously preparing nitrobenzene by nitrating benzene with a mixture of nitric acid and sulfuric acid, in which, during a production shutdown, rather than running the whole production plant down, the production plant is run wholly or at least partly in circulation. The present invention further relates to a plant for preparation of nitrobenzene and to a method of operating a plant for preparation of nitrobenzene.

BACKGROUND

Nitrobenzene is an important intermediate in the chemical industry which is required particularly for preparation of aniline and hence also for preparation of the di- and polyisocyanates of the diphenylmethane series and the polyurethanes based thereon.

The nitration of benzene with nitric acid to give a crude nitrobenzene has already been the subject of numerous publications and patent applications. The processes that are standard nowadays correspond essentially to the concept of adiabatic nitration of benzene by a mixture of sulfuric acid and nitric acid, which is generally referred to as mixed acid. Such a process was claimed for the first time in U.S. Pat. No. 2,256,999 and is described in current embodiments, for example, in EP 0 436 443 B1, EP 0 771 783 B1 and U.S. Pat. No. 6,562,247 B2. It is a particular feature of the processes with an adiabatic reaction regime that no technical measures are taken to supply or remove heat to or from the reaction mixture.

Isothermal processes for nitration of benzene with mixed acid are also known, as described, for example, in EP 0 156 199 B1.

Also known are processes, for example from U.S. Pat. No. 2,739,174 or U.S. Pat. No. 3,780,116, for the nitration of benzene that do not require the use of sulfuric acid.

In principle, gas phase processes for nitration of benzene with nitric acid or nitrogen oxides are also possible, but the yields achievable thereby at the present time are still low (EP 0 078 247 B1, EP 0 552 130 B1).

A common factor to all these processes is that the reaction product formed at first is a crude nitrobenzene typically containing, as impurities, nitric acid and—if nitration has been effected with mixed acid-sulfuric acid, water, benzene and, as organic impurities, dinitrobenzene, nitrated oxidation products of benzene, especially nitrated phenols (nitrophenols). The crude nitrobenzene may also contain organic compounds formed from the compounds that were present as impurities in the benzene used (WO 2008/148608 A1). In addition, the crude nitrobenzene often also contains metal salts that may be present in dissolved form in the acid residues or in the crude nitrobenzene (DE 10 2007 059 513 A1). These impurities are undesirable since they can adversely affect downstream processes in which nitrobenzene is used, for example the preparation of aniline. Suitable work processes which include wash and distillation stages are described, for example, in U.S. Pat. No. 6,288,289 B1, EP 1 593 654 A1, EP 1 816 117 B1 and WO 2011/021057 A1.

The quality of a reaction process for preparation of nitrobenzene is thus defined firstly by the content of unwanted secondary components and impurities in the crude product that arise from improper conduct of the reaction. Secondly, the quality of a reaction process is defined in that the entire process can be operated without technical production outage or problems that necessitate intervention in the process, and that losses of feedstocks are prevented or at least minimized.

Such problems can occur, for example, in the startup and shutdown of the nitration reaction. Problems of this kind may, for example, be that solids are formed that lead to caking and blockage in the equipment (nitration tank, heat exchangers, conduits, etc.). A further disadvantage is that, in the event that inspection, maintenance, repair and cleaning operations are necessary on or in a reactor or another plant section, it is regularly necessary always to switch off all plant sections since the process steps build on one another and hence always proceed successively. As a result, it is necessary to empty the entire plant, which leads to a considerable amount of reject material. Furthermore, energy has to be expended in order to bring reactors and plant sections back to the respective operating temperatures. Such production shutdowns for plant inspections, repair and cleaning measures or shortfalls of raw material or auxiliary that occur, whether planned or unplanned, are recurrent plant states which have a considerable influence on the economic operation of a plant or process that works continuously.

Although the prior art processes described succeed in preparing nitrobenzene with a high yield and without loss of quality in the end products, the only processes described are in the normal state of operation. Production shutdowns for plant inspections and repair and cleaning measures or, for example, shortage of raw material or auxiliary are not taken into account. At the same time, production shutdowns, planned or unplanned, are recurrent plant states which have a considerable influence on the economic operation of a continuously operating plant.

Such a production shutdown may be an inspection shutdown which is planned in advance, for which purpose the plant is run down, the energy supplies are switched off and typically all plant sections that are to be inspected are opened and cleaned for the purpose of examination. Such an inspection may take one or more weeks. After the inspection has ended, the production plant is closed, optionally inertized and provided with auxiliaries and, once the appropriate energy sources and raw materials are available, started up again. However, a production shutdown is not necessarily associated with opening or another mechanical intervention into a reactor or another apparatus in the plant, but may also be connected to the shutdown and restart of the production plant for various other reasons, for example in the event of outage of the raw material supply. In such a case, the plant is typically run in part-load operation and, in the worst case, when the logistical supply chain is interrupted, has to be shut down. Furthermore, production shutdowns may be forced by requirements for maintenance, cleaning or repair in the production plant. Shutdowns here in the nitrobenzene process are typically described as short when production is interrupted for up to one day. It is a feature of all these production shutdowns in practice that there are losses of production, and that, on restarting of the plant, for example when inertization is necessary, nitrogen is consumed or, in the heating of the plant or the feedstocks, forms of energy such as steam and power are required.

The person skilled in the art is aware that an industrial process operated semicontinuously or continuously proceeding from a production plant in operation cannot be switched instantaneously to a production shutdown, but has to be run down in a controlled manner beforehand. This is also the case for a plant outage in the event of an accident. In order to be able to produce again after the production shutdown, the plant has to be run back up to the process parameters before the production shutdown. Reactants and apparatuses have to be heated up, apparatuses may have to be inertized, and the loading of the apparatuses with the reactants is gradually increased to the desired target value. During this startup phase, there is thus still loss of production volume, and a disproportionate amount of energy has to be expended in order to prepare the cooled plant for startup and then to run it up to the desired target value with observation of all operationally relevant parameters as well.

What would thus be desirable would be a process for preparing nitrobenzene in which simple measures enable optimization of production shutdowns in the operation of the nitrobenzene preparation process in terms of time taken, energy consumption, auxiliary and raw material consumption and/or reduction in wastes. This would lead to a not inconsiderable degree of improvement in productivity or economic viability of a continuously operated process or a corresponding production plant.

SUMMARY OF THE INVENTION

It has been found that, surprisingly, this object is achieved for a nitrobenzene preparation process when (expressed in simplified form and without restriction thereto), during a brief shutdown, as many plant sections as possible are put in circulation mode ("on standby"), in order to be able to start up the overall plant again immediately after the measure. It has also been found that, surprisingly, the energy consumption in a plant put in circulation mode for 1 hour for up to 1 day is sometimes smaller than completely shutting down the plant for one day and then starting it up again. By means of a controlled circulation mode in the plant sections that are not affected by the brief shutdown, various advantages are implemented, as is still to be elucidated in detail further down.

The present invention therefore provides the following:

A process, preferably operated adiabatically, for preparing nitrobenzene, comprising the steps of (I) nitrating benzene with nitric acid in sulfuric acid to form nitrobenzene in a reactor, with introduction of benzene with a mass flow rate of $m_1$, nitric acid with a mass flow rate of $m_2$ and sulfuric acid with a mass flow rate of $m_3$ into the reactor;

(II) separating the phases of the reaction mixture from step (I) in a phase separation apparatus into an aqueous sulfuric acid-containing phase and an organic nitrobenzene-containing phase; and optionally (and preferably) steps (III) to (VII):

(III) concentrating the aqueous phase obtained in step (II) by evaporating water in an evaporation apparatus (called the "flash evaporator") to give an aqueous sulfuric acid-containing phase having elevated sulfuric acid concentration, with recycling of the concentrated sulfuric acid-containing aqueous phase via a sulfuric acid tank into step (I) and use thereof as a constituent of mass flow $m_3$;

(IV) washing the organic nitrobenzene-containing phase obtained in step (II) in at least two stages and separating off the aqueous phase after each stage, using a wash vessel having a phase separation unit or a wash vessel and a separate phase separation apparatus in each stage, (V) distilling, preferably rectifying, the organic nitrobenzene-containing phase obtained in the last stage of step (IV) in a distillation apparatus, (VI) working up the wastewater from the first wash stage of step (IV), comprising collecting the wastewater in a wastewater collection vessel and cleaning this wastewater in an apparatus for distillation or stripping, (VII) working up the wastewater from the second wash stage of step (IV), comprising collecting the wastewater in a wastewater collection vessel and cleaning this wastewater in an apparatus for distillation or stripping, where the apparatus for distillation or stripping may be connected up- and/or downstream of an apparatus for thermal pressure decomposition, wherein in the event of shutdown of one or more plant sections from steps (I) to (VII), if they are conducted, the mass flow $m_1$ and the mass flow $m_2$ are reduced to zero and, in at least one of the plant sections that has not been shut down, the output stream is used again as input stream for the respective plant section or an upstream plant section.

The present invention further provides a plant for preparation of nitrobenzene, as is still to be described in detail further down, and which is suitable for the performance of the process of the invention.

Finally, the present invention provides a method of operating a plant for preparation of nitrobenzene, which is still to be described in detail further down.

DETAILED DESCRIPTION

Figure 1:
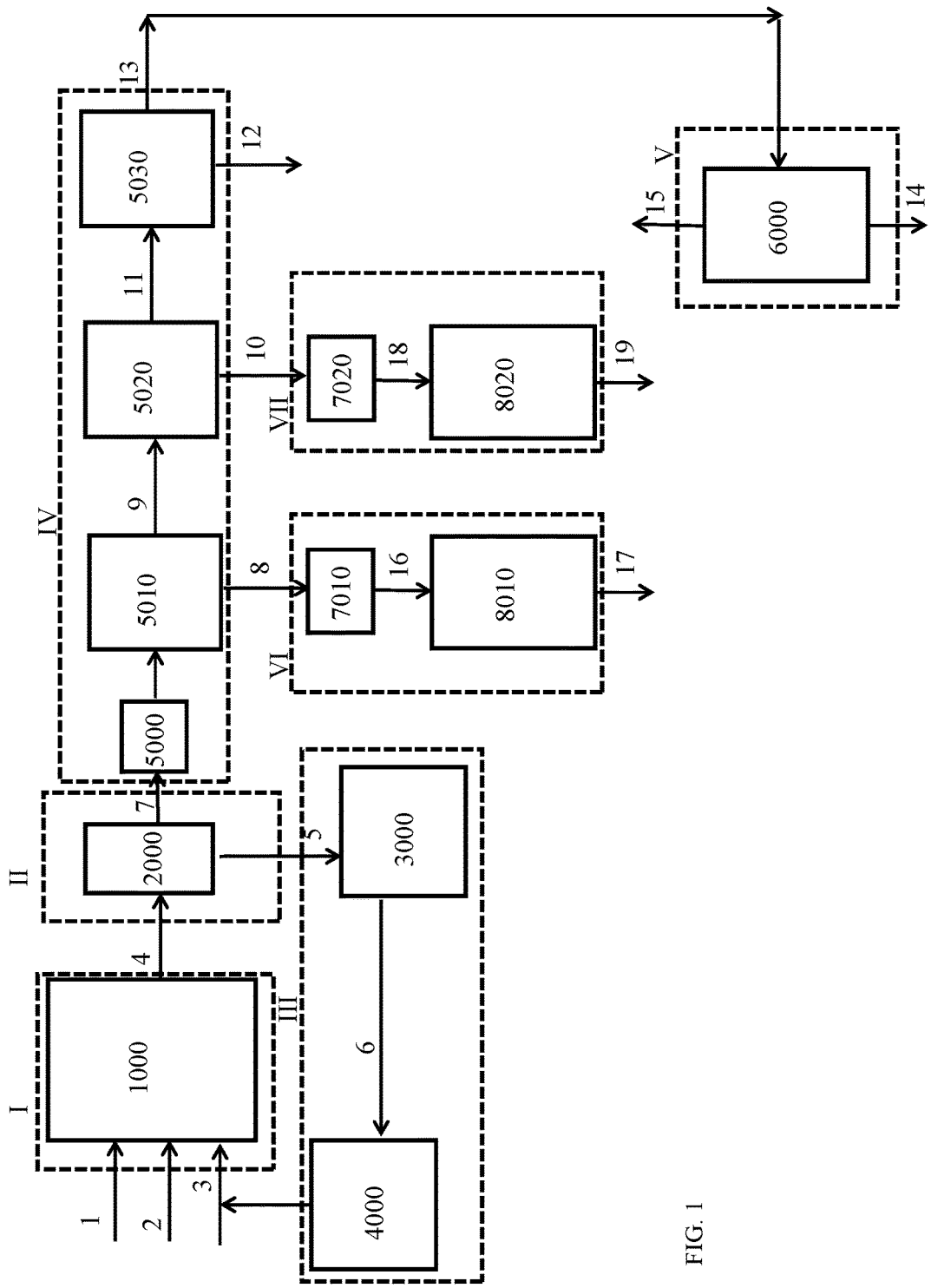
FIG. 1 illustrates an embodiment with three wash stages with process streams in regular operation, without the optional thermal pressure decomposition.

The "shutdown" of a plant section means the stoppage thereof, such that an inspection, repair, maintenance or cleaning measure can be conducted in the plant section. The present invention is thus concerned with those production shutdowns which can be described as "brief shutdowns" for inspection, repair, cleaning or maintenance purposes in sections of the plant or, for example, as a result of a time-limited lack of feedstocks or auxiliaries. The present invention makes it possible to implement such a measure in a plant section without having to shut down the entire production plant. Instead, the present invention enables operation of plant sections not affected by the inspection, repair, maintenance or cleaning measure, or of the corresponding process steps, in "circulation mode". Thus, the complete shutdown of the plant is restricted to exceptional (rare) cases, for instance a complete plant inspection. According to the invention, the term "shutdown" accordingly encompasses, in the case of presence of m plant sections within the meaning of the present invention (in this regard, see also the paragraph which follows), where m is a natural number, the shutdown of a maximum of m−1 of these plant sections. According to the invention, at least one plant section is thus not "shut down" (i.e. "completely stopped"). Preferably, the present invention is concerned with the case of shutdown of 1 to 2 plant sections, more preferably of 1 plant section. According to the invention, therefore, in the case of shutdown of a plant section (or two or more plant sections, but not all plant sections), the formation of further product is always interrupted (since the mass flow rates $m_1$ and $m_2$ are being reduced to zero and, therefore, no further product can be produced). Also encompassed by the invention, however, is the case that the reactor from step (I) is being operated in circulation mode (in this regard, see also the paragraph which follows) and another plant section within the meaning of the above definition is being shut down. "Circulation mode" is understood in the context of this invention to mean that the output stream from a plant section is used as input stream for this plant section or another plant section connected directly or indirectly (i.e. with further plant sections in between) upstream of the plant section in question. In this context, "plant section" means the plant section corresponding to the respective step (I) to (V), if they are conducted, in a plant for preparation of nitrobenzene by the process of the invention.

For example, the plant section from step (I) comprises "a reactor", this term also encompassing embodiments in which two or more reactors (for example a cascade of two or more reactors connected in series) are used (in other words, the word "a" in this connection and in connection with other apparatuses of other plant sections as well should be regarded as the indeterminate article and not to mean the number "one"). Reactors connected in parallel or in series are known in the prior art in the preparation of nitrobenzene as well, and can also bring advantages in particular dimensions and operational characteristics. A plant section may thus comprise two or more apparatuses, i.e. different apparatuses (e.g. wash vessel and phase separation apparatus in step (IV)). The plant section from step (II) comprises a phase separation apparatus, the plant section from step (III) an evaporation apparatus, the plant section from step (IV) comprises, as well as the crude nitrobenzene tank for each wash stage, a wash vessel (either with integrated unit for phase separation or followed by a separate phase separation apparatus), and the plant section from step (V) a distillation apparatus. It will be appreciated that the plant sections, as well as the apparatuses detailed explicitly above, may also include peripheral equipment, for example pumps, heat exchangers and the like.

The circulation mode can also be established over several apparatuses of a plant section. For example, the output stream from the last apparatus of a plurality of apparatuses connected in series in a plant section may be used as input stream for the first apparatus of the apparatuses connected in series in this plant section. It is also possible to apply the circulation mode only to a portion of the apparatuses of a plant section, for example when the output stream from the last apparatus of a plurality of apparatuses connected in series in a plant section is recycled not into the first but into a further apparatus of this plant section.

The circulation mode can also be established over two or more plant sections. For example, the output stream from the last apparatus of a plant section, for example the nitrobenzene stream obtained in the distillation in step (V), can be used as input stream for the first apparatus of an upstream plant section, for example the wash in step (IV), in which case the circulation mode is established in that the output stream from the distillation mentioned by way of example serves as input stream for the wash.

The stopping of $m_1$ and $m_2$, i.e. the mass flows of benzene and nitric acid into the reactor from step (I), ensures that, during the interruption which, as described above, is implemented for the purpose of inspection, maintenance, repair and/or cleaning of a section of the production plant or is caused by a shortage of raw material(s) and/or auxiliary/auxiliaries, the reaction in step (I) does not continue to take place. This, and the use of the output stream from at least one uninterrupted step and corresponding plant section as input stream for the respective step and corresponding plant section or an upstream plant section, ensures that the steps and corresponding plant sections are each run in circulation.

Embodiments of the process of the invention are described hereinafter. They may be combined with one another as desired unless the opposite is clear from the context.

The individual steps of the process of the invention are preferably conducted within a continuous operation.

It is particularly preferable that the process of the invention also comprises steps (III), (IV), (V), (VI) and (VII).

The overall process of nitrobenzene preparation can be subdivided in conceptual terms as follows:

1.) nitration reaction (step (I) and corresponding plant section) with phase separation (step (II) and corresponding plant section) and concentration of the sulfuric acid (step (III) and corresponding plant section),
2.) washes (preferably acidic, alkaline and neutral wash; step (IV) and corresponding plant section),
3.) distillation (step (V) and corresponding plant section) and
4.) optionally (and preferably) acidic wastewater workup (step (VI) and corresponding plant section) and
5.) optionally (and preferably) alkaline wastewater workup (step (VII) and corresponding plant section).

Preferably, step (IV) comprises the steps of (IVa) washing the organic nitrobenzene-containing phase obtained in step (II) in at least one acidic wash, then separating the phases into an aqueous phase and an organic nitrobenzene-containing phase (1st wash stage);
(IVb) washing the organic phase obtained in step (IVa) in at least one alkaline wash with an aqueous solution of a base selected from the group consisting of sodium hydroxide, sodium carbonate and sodium hydrogencarbonate, then separating the phases into an aqueous phase and an organic nitrobenzene-containing phase (2nd wash stage);
(IVc) washing the organic phase obtained in step (IVb) in at least one neutral wash, preferably two to four neutral washes, more preferably two or three neutral washes, most preferably two neutral washes, with water, then separating the phases into an aqueous phase and an organic nitrobenzene-containing phase (3rd wash stage).

In a preferred embodiment, the process of the invention therefore comprises the steps of (I) nitrating benzene with mixtures of nitric acid and sulfuric acid to form nitrobenzene in a reactor, with introduction of benzene with a mass flow rate of $m_1$ and a mixture of nitric acid (mass flow rate of $m_2$) and sulfuric acid (mass flow rate of $m_3$) into the reactor;
(II) separating the phases of the reaction mixture from step (I) in a phase separation apparatus into an aqueous phase and an organic nitrobenzene-containing phase,
(III) concentrating the sulfuric acid-containing aqueous phase from step (II) in an evaporation apparatus to give an aqueous sulfuric acid-containing phase having elevated sulfuric acid concentration, with recycling of the concentrated sulfuric acid-containing aqueous phase via a sulfuric acid tank into step (I) and use thereof as a constituent of mass flow $m_3$;

(IV) washing the organic nitrobenzene-containing phase obtained in step (II) in at least two stages, using a wash vessel having a phase separation unit or a wash vessel and a separate phase separation apparatus in each stage, comprising (IVa) washing the organic nitrobenzene-containing phase obtained in step (II) in at least one wash, preferably one or two washes, more preferably one wash (called "acidic wash(es)"), then separating the phases into an aqueous phase and an organic nitrobenzene-containing phase, (IVb) washing the organic nitrobenzene-containing phase obtained in step (IVa) in at least one alkaline wash, preferably one or two alkaline washes, more preferably one alkaline wash, with an aqueous solution of a base selected from the group consisting of
sodium hydroxide, sodium carbonate and sodium hydrogencarbonate,
then separating the phases into an aqueous phase and an organic nitrobenzene-containing phase, (IVc) washing the organic nitrobenzene-containing phase obtained in step (IVb) in at least one neutral wash, preferably two to four neutral washes, more preferably two or three neutral washes, most preferably two neutral washes, with water, then separating the phases into an aqueous phase and an organic nitrobenzene-containing phase, (V) distilling, preferably rectifying, the organic nitrobenzene-containing phase obtained in step (IVc) to obtain purified nitrobenzene, (VI) working up the wastewater obtained in step (IVa), comprising collecting the wastewater in a wastewater collection vessel and cleaning this wastewater in an apparatus for distillation or stripping, and (VII) working up the wastewater from step (IVb), comprising collecting the wastewater in a wastewater collection vessel and cleaning this wastewater in an apparatus for distillation or stripping, where the apparatus for distillation or stripping may be connected up- and/or downstream of an apparatus for thermal pressure decomposition, wherein, in the event of shutdown of one or more plant sections from steps (I) to (VII), the mass flow $m_1$ and the mass flow $m_2$ are reduced to zero and, in at least one of the plant sections that has not been shut down, the output stream is used again as input stream for the respective plant section or an upstream plant section.

Thermal pressure decomposition is understood here to mean a process for workup of alkaline wastewater in which organic impurities are decomposed under the action of elevated pressure and elevated temperature. Suitable processes are known to those skilled in the art and are described, for example, in EP 1 593 654 B1. In the context of the present invention, it is especially preferable to heat the alkaline wastewater (optionally pretreated in the apparatus for distillation or stripping), with exclusion of oxygen, to temperatures of 150° C. to 500° C. under an absolute pressure of 50 bar to 350 bar.

The appended drawing FIG. 1 shows an embodiment with three wash stages (without the optional thermal pressure decomposition) with process streams in regular operation:

Benzene (1), nitric acid (2) and sulfuric acid (3) are converted in a reactor (1000). The process product of this step (I), stream 4, is separated in a phase separation apparatus (2000) into an aqueous phase (5) and an organic nitrobenzene-containing phase (7) (step (II)). The aqueous phase (5) consisting essentially of dilute sulfuric acid is concentrated in an evaporation apparatus (3000) (step (III)). The concentrated sulfuric acid-containing phase thus obtained is recycled via a sulfuric acid tank (4000) into the reactor (1000) from step (I) and used as a constituent of mass flow $m_3$. The organic phase (7) obtained in step (II) is fed via a crude nitrobenzene tank (5000) to the individual wash stages (5010-"acidic wash"; 5020-"alkaline wash"; 5030-"neutral wash"), without showing the wash liquid streams supplied for the sake of simplicity. This gives the wastewater streams 8, 10 and 12 and the washed organic nitrobenzene-containing phase 13 (step (IV) with component steps (IVa), (IVb) and (IVc)). The organic phase 13 is purified in a distillation apparatus (6000) (step (V)), drawing off low boilers (essentially unconverted benzene) overhead (stream 15) and nitrobenzene at the bottom (stream 14). This low boiler removal may be followed by a further distillative purification stage (not shown) in which stream 14 is drawn off overhead or as a sidestream for removal of high-boiling impurities.

The wastewater 8 from the first wash stage (IVa) is fed (stream 16) via a wastewater collecting vessel (7010) to a purifying apparatus (8010), giving cleaned wastewater (17) (step (VI)). This apparatus 8010 is an apparatus for distillation or stripping. The wastewater 10 from the second wash stage (IVb) is fed (stream 18) via a wastewater collecting vessel (7020) to a purifying apparatus (8020), giving cleaned wastewater (19) (step (VII)). This apparatus 8020 is an apparatus for distillation or stripping. As already mentioned, the apparatus 8020 may be connected up- and/or downstream of an apparatus for thermal pressure decomposition (not shown in FIG. 1). The wastewater 12 from the third wash stage (IVc) can, as known from the prior art, be disposed of or used further (not shown in FIG. 1).

The embodiment described relates especially to the case of a brief shutdown in production of 1 hour up to 1 day. The procedure of the invention allows the production plant to be operated completely or partly in circulation mode of individual plant sections. It is particularly preferable here to conduct the circulation mode in each case over the above-defined constituents of the process for nitrobenzene preparation. This means that (1) the nitration reaction with phase separation and concentration of the sulfuric acid, (2) the washes (acidic, alkaline and neutral wash), (3) the distillation and (4) acidic wastewater workup and (5) the alkaline wastewater workup are each put in circulation mode.

Figure 2:
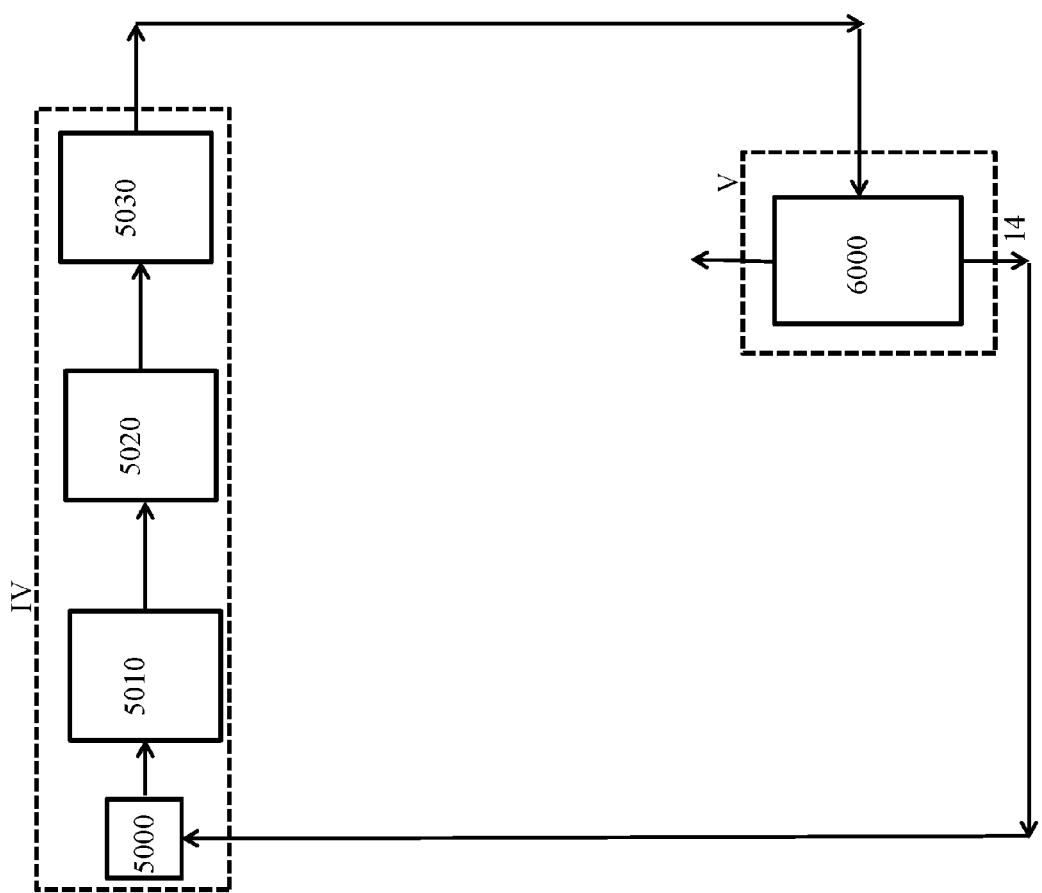
FIG. 2 illustrates an embodiment of the invention circulation mode in which (IV) and (V) operate together such that the output stream from (IV) forms the input stream for (V) and the output stream from (V) forms the input stream for (IV).

It is preferable here when, at least in steps (IV) and (V), the output streams are used again as input streams for the corresponding plant sections. This may also include use of the output stream from step (IV) again as input stream for this step, and running step (V) in exactly the same way. Alternatively, however, it is also possible to operate steps (IV) and (V) together in circulation mode, meaning that the output stream from step (IV) forms the input stream for step (V), and the output stream from step (V) forms the input stream for step (IV). This procedure is shown in schematic and highly simplified form in FIG. 2. For example, the distillation can be put in circulation together with the wash, in that the output from the distillation (nitrobenzene) goes into the crude nitro tank and thence through the washes back to the distillation.

In this context, it is especially preferable when, in the event of interruption of the process in at least one of steps (I) to (VII) (i.e. the shutdown of one or more plant sections from steps (I) to (VII)), with step (IV) comprising the abovementioned component steps, the output stream in every other step (I) to (VII), i.e. every other step not affected by the interruption, is used again as input stream for the respective plant section. In this way, the effects of the invention are manifested to a particularly advantageous degree.

The present invention further provides a plant for preparation of nitrobenzene, comprising the plant sections of:
(I) a reactor for nitration of benzene with a mixture of nitric acid and sulfuric acid to form nitrobenzene,
(II) a phase separation apparatus for phase separation of the reaction mixture obtained in the reactor (I) into an aqueous sulfuric acid-containing phase and an organic nitrobenzene-containing phase, and optionally (and preferably) plant sections (III) to (VII):
(III) an evaporator (III.a) for concentration of the aqueous sulfuric acid-containing phase and a sulfuric acid reservoir tank (III.b) for accommodation of the concentrated aqueous sulfuric acid-containing phase and the provision thereof for the reactor (I),
(IV) a wash vessel with phase separation unit per wash stage or a wash vessel and a separate phase separation apparatus per wash stage for at least two-stage washing of the organic nitrobenzene-containing phase from (II),
(V) a distillation apparatus for purification of the organic nitrobenzene-containing phase from (IV),
(VI) a wastewater collection vessel and an apparatus for distillation or stripping for collection and subsequent cleaning of the wastewater from the first wash stage from (IV),
(VII) a wastewater collection vessel and an apparatus for distillation or stripping which may be connected up- and/or downstream of an apparatus for thermal pressure decomposition, for collection and subsequent cleaning of the wastewater from the second wash stage from (IV),
wherein
the plant is configured such that, in the event of shutdown of one or more plant sections (I) to (VII), if they are present, no further introduction of benzene and nitric acid into the reactor (I) takes place and, independently of one another or simultaneously, in at least one plant section unaffected by the shutdown, the output stream is recycled and used as input stream for the respective plant section or an upstream plant section. The configuration of the plant in such a way that "in the event of shutdown of one or more plant sections (I) to (VII), if they are present, no further introduction of benzene and nitric acid into the reactor (I) takes place" should be understood to mean that, prior to or simultaneously with the shutdown of a plant section, the supply of benzene and nitric acid is interrupted; in other words, prior to or simultaneously with the establishment of circulation mode in at least one plant section unaffected by the shutdown, the supply of benzene and nitric acid is interrupted. In terms of apparatus, this can be implemented in various ways, for example through the incorporation of process control units which automatically interrupt the supply of benzene and nitric acid on shutdown of one or more plant sections (on setting of one or more plant sections that are not to be shut down to circulation mode). The setting-up of a barrier circuit which enables the setting to circulation mode only in the event of interrupted supply of benzene and nitric acid is likewise conceivable. Suitable software and hardware products are commercially available and known to those skilled in the art. Any necessary programming and adaptation operations are within the routine duty which is customary to the person skilled in the art.

It will be apparent that this plant is especially configured to be able to conduct the process of the invention therein. Thus, the advantages and effects of the process of the invention also apply to the plant of the invention.

More preferably, plant section (IV) comprises:
(IVa) a wash vessel with phase separation unit or a wash vessel and a separate phase separation apparatus for washing and subsequent phase separation of the organic nitrobenzene-containing phase from (II),
(IVb) a wash vessel with phase separation unit or a wash vessel and a separate phase separation apparatus for washing and subsequent phase separation of the organic nitrobenzene-containing phase from (IVa),
(IVc) a wash vessel with phase separation unit or a wash vessel and a separate phase separation apparatus for washing and subsequent phase separation of the organic nitrobenzene-containing phase from (IVb).

It is especially preferable here that, independently of one another or simultaneously, the output mass flow in every other plant section unaffected by the interruption is recycled and used again as input mass flow for the respective plant section or an upstream plant section. Thus, in the plant sections unaffected by the interruption, at least one circulation mode is conducted.

Should two or more nitration reactor lines be operated in parallel, it is firstly possible to operate one reactor line in the circulation mode of the invention and to set the other reactor lines successively to the circulation mode of the invention. Alternatively, however, it is also possible in the context of the present invention to transfer all nitration reactor lines simultaneously or essentially simultaneously to the circulation mode of the invention. Likewise encompassed by the processes and the plant according to the present invention are cases in which 3 or 4 reactor lines go into 1 or 2 phase separation apparatuses, 1 or 2 phase separation apparatuses go into 2 flash evaporators, and the sulfuric acid that flows away from the latter is optionally guided into a sulfuric acid reservoir. The organic phase that emerges from the phase separation apparatus can be worked up, for example, in a single-line wash with distillation.

Examples of different circulation modes are listed hereinafter:
1.) In the nitration reaction with phase separation and concentration of the sulfuric acid, consisting of nitrators with sulfuric acid circulation pumps, phase separators, flash evaporators with vacuum pumps and condensers and sulfuric acid reservoir, the benzene stream and nitric acid stream are stopped at the same time. The circulating sulfuric acid can then be pumped under reaction starting conditions (preferably 101° C.) by means of the sulfuric acid circulation pumps through the nitrators, phase separation, flash evaporator (sulfuric acid concentration) into the sulfuric acid reservoir and thence in a circuit back to the nitrators for several hours.
2.) In the washes, consisting of a crude nitrobenzene tank and an acidic, alkaline and neutral wash, the crude nitrobenzene stream from the phase separation apparatus to the crude nitro tank is interrupted. The washed crude nitrobenzene can then be pumped from the neutral wash to the crude nitro tank, through the acidic wash and alkaline wash and back to the neutral wash in circulation for an indeterminate period. The wash water is run in countercurrent into the neutral wash through the alkaline wash to the alkaline wastewater workup. In the course of this, the flow rate of the crude nitrobenzene from the crude nitrobenzene tank to the acidic wash and of the wash water to the neutral wash is reduced to minimal load.

3.) In the distillation, consisting of a heat exchanger, nitrobenzene column with bottoms withdrawal of the nitrobenzene end product and a natural circulation evaporator, vapor condensers with vacuum pumps, vapor phase separation apparatus and return benzene reservoir with pump, after the reaction has been stopped, no further crude nitrobenzene occurs in the washes. The bottoms output from the nitrobenzene column is sent back to the crude nitrobenzene tank through the heat exchanger and hence circulated through all the washes and through the nitrobenzene column. The vapors obtained (benzene and water) are condensed and separated in the vapor phase separation apparatus into an aqueous phase and an organic phase. The benzene-containing organic phase is likewise conducted to the crude nitrobenzene tank. The aqueous phase is disposed of via the acidic wash and the acidic wastewater workup (the vacuum system remains in operation). The circulation mode can be operated for an indefinite period.

4.) In the acidic wastewater workup, consisting of a wastewater reservoir tank, a heat exchanger, a wastewater distillation with condensation system, a wastewater cooler and outlet to the acidic wash, after the nitration has been shut down, no further acidic wastewater occurs. The wastewater distillation can be operated with steam for an indefinite period, in which case the acidic wastewater in the bottoms from the wastewater column is put in circulation mode to the wastewater reservoir tank and the vapors obtained are run to the acidic wash.

5.) In the alkaline wastewater workup, consisting of a wastewater reservoir tank, a heat exchanger, a wastewater distillation with condensation system and an outlet to a plant for thermal pressure decomposition (TDZ), after the alkaline wash has been shut down, no further alkaline wastewater occurs. The wastewater distillation can be operated with steam for an indefinite period, in which case the alkaline wastewater in the bottoms from the wastewater column is put in circulation mode to the wastewater reservoir tank and the vapors obtained are run to the acidic wash. The TDZ, consisting of a wastewater reservoir with high-pressure pump, heat exchanger, steam heater, dwell tube and cooler, may be operated with steam for an indefinite period, in which case the alkaline wastewater from the exit of the TDZ is put in circulation mode to the wastewater reservoir.

These examples are of course merely representative of a multitude of possible circulation modes, the exact configuration of which depends on the specific circumstances in a production plant and therefore cannot be generalized. However, a feature common to all conceivable circulation modes is that no product leaves the plant when the plant is a single nitrobenzene line.

Should two or more nitrobenzene reactor lines be operated in parallel, it is possible but not obligatory for product to leave the plant when, for example, the plant is being run with partial load.

The present invention further provides a method of operating a plant for preparation of nitrobenzene, comprising the plant sections of:

(I) a reactor for nitration of benzene with a mixture of nitric acid and sulfuric acid to form nitrobenzene, (II) a phase separation apparatus for phase separation of the reaction mixture obtained in the reactor (I) into an aqueous sulfuric acid-containing phase and an organic nitrobenzene-containing phase, and optionally (and preferably) plant sections (III) to (VII):

(III) an evaporator (III.a) for concentration of the aqueous sulfuric acid-containing phase and a sulfuric acid reservoir tank (III.b) for accommodation of the concentrated aqueous sulfuric acid-containing phase and the provision thereof for the reactor (I), (IV) a wash vessel with phase separation unit per wash stage or a wash vessel and a separate phase separation apparatus per wash stage for at least two-stage washing of the organic nitrobenzene-containing phase from (II), plant section (IV) more preferably comprising the above-defined constituents (IVa), (IVb) and (IVc), (V) a distillation apparatus for purification of the organic nitrobenzene-containing phase from (IV), (VI) a wastewater collection vessel and an apparatus for distillation or stripping for collection and subsequent cleaning of the wastewater from the first wash stage from (IV), (VII) a wastewater collection vessel and an apparatus for distillation or stripping which may be connected up- and/or downstream of an apparatus for thermal pressure decomposition, for collection and subsequent cleaning of the wastewater from the second wash stage from (IV), wherein shutdown of one or more plant sections (I) to (VII), if they are present, is accomplished by running through the following steps:

(i) stopping the supply of benzene and nitric acid and optionally sulfuric acid into the reactor (I);

(ii) running at least one plant section in such a way that the output stream from the respective plant section is used as input stream for the respective plant section or an upstream plant section (circulation mode);

(iii) shutting down at least one plant section.

Especially preferably, the plant is the plant of the invention for preparation of nitrobenzene.

In a preferred embodiment, this method of the invention comprises the further steps of:

(iv) optionally opening the at least one plant section shut down in step (iii);

(v) conducting a maintenance, cleaning, inspection and/or repair measure;

(vi) optionally closing and optionally inertizing the at least one plant section from step (v);

(vii) starting up the at least one plant section from step (vi);

(viii) starting the supply of benzene and nitric acid into the reactor (I).

More preferably, every plant section which has not been run down (shut down) is switched to circulation mode and hence the advantages and effects of the present invention are advantageously achieved.

In a plant of the invention, the process of the invention can be conducted, for example, as follows:

In the first step, the input streams of benzene and nitric acid are stopped at the same time. The circulating sulfuric acid can then be sent under reaction starting conditions (preferably 101° C.) by means of the sulfuric acid circulation pumps through the nitrators, phase separation, flash evaporator (sulfuric acid concentration) into the sulfuric acid reservoir and thence in a circuit back to the nitrators.

In the second step, once the washed crude nitrobenzene from the neutral wash is being conducted to the crude nitro tank, through the acidic wash and alkaline wash and back to the neutral wash, the washes are put in circulation mode.

In the third step, the distillation is put in circulation mode together with the washes.

In the fourth step, the acidic wastewater workup is put in circulation mode.

In the fifth step, the alkaline wastewater workup comprising wastewater column and TDZ is put in circulation mode.

The plant section affected, for example, by a maintenance measure is run down, emptied, cleaned and optionally opened for the pending measure. Then the maintenance measure is conducted and the plant section is closed again, inertized and charged with auxiliaries and feed materials, and prepared for startup.

In order to start up the plant again, first the acidic wastewater workup, the washes with distillation and then the nitration is put into operation. The alkaline wastewater workup is put in operation as required, since it is decoupled from the rest of the plant by means of a buffer tank (wastewater reservoir tank).

The restarting of the plant from circulation mode can be conducted, for example, as follows:

1.) In the acidic wastewater workup, consisting of a wastewater reservoir tank, a heat exchanger, a wastewater distillation with condensation system, a wastewater cooler and outlet to the acidic wash, after the nitration has been shut down, acidic wastewater occurs again. The wastewater distillation is put in operation by sending the acidic wastewater in the bottoms from the wastewater column to the wastewater conduit.

2.) In the washes, consisting of a crude nitrobenzene tank and an acidic, alkaline and neutral wash, the crude nitrobenzene from the crude nitrobenzene tank is run into the acidic wash, through the alkaline wash to the neutral wash. The crude nitrobenzene leaving the neutral wash is sent to the distillation. The wash water is run in countercurrent into the neutral wash through the alkaline wash to the alkaline wastewater workup. In the course of this, the flow rate of the crude nitrobenzene from the crude nitrobenzene tank to the acidic wash and of the wash water to the neutral wash is run up to startup load.

3.) In the distillation, consisting of a heat exchanger, nitrobenzene column with bottoms withdrawal of the nitrobenzene end product and a natural circulation evaporator, vapor condensers with vacuum pumps, vapor phase separation apparatus and return benzene reservoir with pump, crude nitrobenzene occurs again. The bottoms output from the nitrobenzene column is sent through the heat exchanger to the end product tank. The vapors obtained (benzene and water) are condensed and separated in the vapor phase separation apparatus into an aqueous phase and an organic phase. The benzene-containing organic phase is conveyed to the return benzene tank. The aqueous phase continues to be disposed of via the acidic wash and the acidic wastewater workup.

4.) In the nitration reaction with phase separation and concentration of the sulfuric acid, consisting of nitrators with sulfuric acid circulation pumps, phase separation apparatus, flash evaporator with vacuum pumps and condensers and sulfuric acid reservoir, the circulating sulfuric acid continues to be run back into the sulfuric acid reservoir through the nitrators, phase separation and flash evaporator (sulfuric acid concentration) under reaction starting conditions (preferably 101° C.) by means of the sulfuric acid circulation pumps. At the same time, the benzene stream and nitric acid stream are switched on. The crude nitrobenzene obtained in the phase separation apparatus is fed to the crude nitrobenzene tank.

5.) In the alkaline wastewater workup, consisting of a wastewater reservoir tank, a heat exchanger, a wastewater distillation with condensation system and an outlet to a plant for thermal pressure decomposition (TDZ), after the alkaline wash has been started up, alkaline wastewater occurs again. The alkaline wastewater in the bottoms from the wastewater column is sent to the TDZ, and the vapors obtained continue to be run to the acidic wash. The TDZ, consisting of wastewater reservoir with high-pressure pump, heat exchanger, steam heater, dwell tube and cooler, is then charged with stripped alkaline wastewater and the output from the TDZ is sent to the wastewater conduit.

The complete nitrobenzene plant is now running with reduced load (startup load) and can now be run up to the desired target production.

It is particularly preferable here to run up the production plant with reduced load, since the required temperature profiles for the nitration, washes, wastewater workup and distillation are otherwise not available quickly enough, which could lead to incomplete nitration with increased by-products and more difficult workup conditions.

The changeover to circulation mode can be conducted, for example, for the nitration reaction with phase separation and concentration of the sulfuric acid, washes (crude nitrobenzene tank, acidic, alkaline and neutral wash), distillation and acidic wastewater workup and alkaline wastewater workup as follows:

The overall plant is run down in a first step (step a)) by stopping the benzene feed and nitric acid feed to the nitration reactor. Circulating sulfuric acid continues to circulate, and the crude nitrobenzene still being formed in the nitration reactor is flushed into the phase separation apparatus. The phases are separated therein and residual crude nitrobenzene is discharged to the crude nitrobenzene tank. In the flash evaporator, the circulating sulfuric acid is freed of residual organics and kept at starting temperature (about 101° C.) by means of steam.

In step b) thereafter, the washes are switched to circulation mode, with the crude nitrobenzene stream and the wash water stream being set to minimal load.

In step c) subsequently, the distillation is switched to circulation mode with retention of the vacuum.

In step d), after the reaction has been stopped, the acidic wastewater workup is switched to circulation mode.

In step e), after the washes from step b) have been shut down, the alkaline wastewater workup (including TDZ) is switched to circulation mode.

In step f), the plant section affected by the brief shutdown is briefly shut down and the brief shutdown measure is conducted.

In step g), the plant section affected by the brief shutdown is made ready for operation again.

Subsequently, in step h), the overall plant is run up again from circulation mode and then brought to the desired target load.

The process of the invention gives rise to the following advantages:
i) Increase in productivity, because the availability of the plant increases, since the time taken for the running down and restarting of the plant for the production shutdown is greatly minimized.

ii) Absence of capital costs for a greater plant capacity and associated maintenance costs.
iii) It is possible to work with a smaller end product tank, since less buffer volume is needed. As a result, lower capital costs and maintenance costs for the end product tank also arise.
iv) In many cases, energy savings arise because there is no need for the preparations required for the shut-down plant sections that are needed for the restart, such as the heating of the auxiliaries and feedstocks or the heating of the equipment etc.
v) Saving of auxiliaries such as steam condensate and nitrogen.
vi) The susceptibility of the pumps to need repair, specifically in the nitration region, and of the vacuum pumps is improved since the slip-ring seals thereof suffer from every restart of the pumps when they are switched off in the event of a shutdown. Thus, subsequent repairs are avoided, which again has a positive effect on the productivity of the plant and maintenance costs.
vii) Avoidance of superfluous waste products, for example excess benzene, excess nitric acid or nitric acid/sulfuric acid mixtures, nitrated oxidation products of benzene and mixtures with crude products or wastewater, which additionally have to be purified, and which arise when the plant has to be subjected to a complete new startup.

The success of the procedure of the invention is surprising to the person skilled in the art because, in principle, in order to save energy and to be able to concentrate on the maintenance measures due in the production shutdown, the skilled person would be much more likely to shut down the entire plant, especially since additional capital costs for recycling pipelines including pumps, retrofitting in the apparatuses and additional process control technology have to be accepted for the process of the invention and for the plant of the invention.

The present invention is to be illustrated hereinafter by examples.

EXAMPLES

Content figures in ppm or % are parts by mass based on the total mass of the respective material/stream. Analysis values, unless stated otherwise, have been determined by means of gas chromatography.

General Conditions for the Preparation of Nitrobenzene in a "Run-In" Production Plant At a production load of 50 t/h of nitrobenzene, a sulfuric acid stream, a nitric acid stream, a fresh benzene stream and a return benzene stream were metered into a nitration reactor. A 5% to 10% excess of benzene was used, based on nitric acid. On completion of conversion of the nitric acid with the benzene to give nitrobenzene in an adiabatic reaction regime, the reaction product, now at about 130° C., was fed to a phase separation apparatus in which the reaction product separated into an organic phase (=crude nitrobenzene, also containing benzene as well as nitrobenzene) and an aqueous phase (=waste acid, also containing small proportions of nitrobenzene and benzene as well as sulfuric acid). The aqueous phase comprising mainly sulfuric acid was subjected to a flash evaporation of water by abruptly lowering the pressure in the evaporator, and concentrated in this way. The concentrated sulfuric acid was stored in the sulfuric acid tank for reuse. After being removed in the phase separation apparatus, the crude nitrobenzene was cooled down to about 50° C. in the crude nitrobenzene cooling operation and sent to the washing operation. This wash comprised an acidic wash stage, an alkaline wash stage and a neutral wash stage.

The stream of purified crude nitrobenzene which has been substantially freed of nitrophenols and salts and has been obtained in this way was heated up again and, in a distillation column, freed of water, benzene and other low boilers which were removed overhead, giving dried pure nitrobenzene. The condensed top product from the distillation column was fed to a phase separation apparatus in which the top product separated into an organic phase (comprising benzene) and an aqueous phase. The organic phase was stored intermediately in a buffer tank and thence run back, as already described above, into the feed of the nitration reactor for reaction. The power consumption of such a plant is about 890 kW/h.

The wastewater obtained in the alkaline wash was worked up as follows:

The wastewater from the alkaline wash was run into a settling tank in which undissolved benzene and nitrobenzene were separated out. 3.5 tonnes per hour of alkaline wastewater which had a nitrobenzene content of 2870 ppm, a benzene content of 409 ppm and a nitrophenols content of 11 809 ppm and a pH of 12.8 (1.8% excess of NaOH compared to the starting content of nitrophenols prior to the alkaline wash) were conducted into a stripping column in order to remove benzene and nitrobenzene from this alkaline wastewater overhead by stripping with steam. For this purpose, 500 kg/h of 6 bar steam were used. The pressure in the top of the column was 1.05 bar (absolute), and the temperature was 99.5° C. The top of the stripping column was equipped with a vertical condenser in which the benzene- and nitrobenzene-containing vapors were condensed out, then recycled into the acidic wash. The moist offgas at 99° C. from the stripping column was connected directly to the condenser and was sprayed with acidic water at 30° C. from the acid water tank. This prevents the possible deposition of ammonium nitrate and/or ammonium nitrite, which can form in the dry region of a conventional offgas conduit used for the separate conduction of the offgas out of the condenser (the ammonium salts mentioned may form from ammonia and nitrogen oxides present in the alkaline wastewater). The acidic water was fed to the acidic wash together with the condensed vapors. Any malfunction of the stripping column can be monitored, for example, by means of redundant safety devices. After the stripping, an alkaline wastewater that contained benzene only in a concentration of up to 10 ppm and nitrobenzene in a concentration of up to 10 ppm was obtained. Subsequently, the alkaline wastewater thus treated was treated in a plant for thermal pressure decomposition with a residence time of 20 min, a temperature of 290° C. and an absolute pressure of 90 bar. The wastewater that arose here was cooled down to 80° C. Thereafter, the wastewater was stripped with direct steam. In the bottoms from the stripping column, a stream of 4.0 tonnes per hour was obtained at an absolute pressure of 1.02 bar, which contained essentially water, ammonia, carbon dioxide and organics. The top product was condensed and cooled down to 35° C. A purge stream of organics was discharged from the condensate. 0.25 tonne per hour of the aqueous condensate stream depleted of organics was recycled into the stripping column as reflux. The proportion of organics in the wastewater obtained, which was sent to a biological water treatment plant, was 4726 ppm. The ammonium content in the wastewater was less than 87 ppm. There were no problems at all with deposits in the region of the offgas from the stripping column.

Nitrobenzene prepared in this way typically has a purity of about 99.96% (GC), a residual benzene content of 0.0028% (GC), a 1,3-dinitrobenzene content of 0.0273% (GC) and a nitrophenol content of <5 ppm (HPLC). In addition, nitrobenzene has a water content of 0.0079% (determined according to Karl Fischer).

Example 1 (Comparative Example): Brief Shutdown of a Production Plant with Complete Stoppage of the Plant, Cleaning Measure and Restarting of the Plant The brief shutdown of the plant served for conduction of cleaning operations in the nitration region. For this purpose, the plant was run down completely, i.e. nitration, washes, distillation, acid water workup and alkaline wastewater workup. The energy supplies were switched off during the cleaning operations. After the cleaning operations, the plant was started up again, for which it was necessary to inertize, fill and heat the entire plant beforehand.

Procedure for the Complete Stoppage of the Plant:

First, the nitration was shut down: The metering pumps for the input streams of benzene and nitric acid were switched off. The vapor from the flash evaporator was stopped 5 minutes after the benzene and nitric acid raw materials. The circulation of sulfuric acid continued for 1 hour until all organics had been discharged from the nitration circuit consisting of nitrators, phase separation apparatus, flash evaporator and circulating sulfuric acid reservoir tank. Then the circulation of sulfuric acid at 100° C. was interrupted by switching off the circulation pump. The nitrators, the phase separation apparatus and the flash evaporator were left under standing sulfuric acid. The remaining circulating sulfuric acid was in the sulfuric acid reservoir tank. The total inventory of sulfuric acid was 74 tonnes. Simultaneously with the circulation pump, the vacuum pump to the flash evaporator was switched off and the vacuum was broken with nitrogen. The nitration circuit was then at rest. Time taken 2 hours, without breaking the vacuum 1 hour.

Thereafter, the acid water workup was shut down by interrupting the feed of acidic wastewater from the acid water reservoir tank to the acid water stripper. The steam to the acid water stripper and the bottoms pump of the stripper were stopped. The acid water workup was then at rest. The time taken was 5 minutes.

Next, the washes were shut down by interrupting the crude nitrobenzene feed from the crude nitrobenzene tank to the acidic wash. The crude nitrobenzene pathway through the acidic, alkaline and neutral wash was stopped by stopping the delivery pumps for the crude nitrobenzene upstream of the respective washes. The washes had an operating temperature of 48° C. and remained filled with crude nitrobenzene. At the same time, the acidic, alkaline and neutral wash water pathway was stopped by switching off the respective pumps. The time taken was 5 minutes.

Then the distillation was shut down by interrupting the feed of crude nitrobenzene and taking away the steam to the distillation column. Immediately thereafter, the product discharge was interrupted by switching off the bottoms pump and the return stream at the top of the column was stopped by stopping the benzene pump. After the vacuum pump had been switched off and vented with nitrogen, the distillation was at rest. The time taken was 5 minutes.

Lastly, the alkaline wastewater workup was shut down by setting the thermal pressure decomposition to circulation mode and stopping the steam to the pressure decomposition. At the same time, the supply and removal of the alkaline wastewater to and from the stripper was stopped by switching off the wastewater pumps and stopping the steam to the stripper. The time taken was 5 minutes. The circulation mode of the thermal pressure decomposition (TDZ) was stopped after 10 hours, as soon as the circulation water had been cooled below 100° C.

The complete stoppage took a total of two hours without purging and emptying of the apparatuses, pumps and pipelines, neglecting the running-down of the TDZ. In modern automated production plants, the number of personnel required for the running-down operation only plays a minor role.

Procedure for the Cleaning Measure:

It was necessary to clear a blockage in the benzene preheater in the feed of the crude nitrobenzene from the phase separation apparatus to the crude nitro tank: First of all, the level in the phase separation vessel was lowered by 50%, in order that no further organic material could run into the benzene preheater to be cleaned. Subsequently, the benzene preheater was purged with condensate through a purging stub mounted between the phase separation apparatus and benzene preheater for 1 hour, in order to remove crude nitrobenzene and traces of sulfuric acid. The purge condensate was led off to the acidic wash. Thereafter, the benzene preheater was mechanically divided from the inlet and outlet, and black precipitates in the benzene preheater that constituted the blockage were rinsed out with large amounts of condensate using two further purging stubs to the water treatment plant. The time taken was 3 hours. After all 3 purging stubs had been disassembled, the inlet and outlet of the benzene preheater were mounted. The time taken for this was 2 hours. Thereafter, the pipelines affected were heated up and cooled down several times, in the course of which the flange connections were re-tightened with the new seals. The time taken was 2 hours.

The cleaning measure took a total of 8 hours. In modern automated production plants, the number of personnel required for the preparation for the cleaning measure, namely partial emptying of the plant, mounting of the purging stub for preliminary cleaning of the benzene preheater with inlet and outlet and subsequent preliminary cleaning with condensate, plays an important role. In this case, one additional production worker is required. Workmen for the disassembly and assembly of the pipelines for the cleaning measure and the cleaning personnel themselves are likewise required.

Procedure for the Restarting of the Plant:

The vacuum pumps in the entire production plant were put in operation beforehand. The phase separation apparatus and the cleaned benzene preheater were inertized with 100 m$^3$ (STP) of nitrogen.

Firstly, the washes were started by starting the crude nitrobenzene pump to put the crude nitrobenzene supply from the crude nitrobenzene tank to the acidic wash into operation. Thereafter, the acidic, alkaline and neutral wash water pathway was started by switching on the respective pumps. Then the crude nitrobenzene pathway through the acidic, alkaline and neutral wash was started by switching on the delivery pumps for the crude nitrobenzene upstream of the respective washes. The washing apparatuses that were filled with crude nitrobenzene and wash water were at 45° C. and warmed gradually back up to 48° C. after the production plant had been started.

Once the last stage of the neutral wash had been put in operation by feeding in 3 t/h of condensate, the distillation was started by applying vacuum to the distillation column and running crude nitrobenzene at 45° C. from the last neutral wash to the distillation column. Thereafter, the bottoms pump of the column was started and crude nitrobenzene was run to the crude nitrobenzene tank. Then the distillation column was supplied with 2 t/h of 16 bar steam and heated up to 170° C. At 50° C. at the top of the column, the reflux was put in operation by starting the benzene pump. The washes and the distillation were ready for restarting of the production plant after 4.5 hours.

In parallel to the washes and the distillation, the acid water workup was started by applying 1 t/h of 6 bar steam to heat up the acid water stripper and starting the bottoms pump of the stripper. Subsequently, the feeding of the acidic wastewater from the acid water reservoir tank to the acid water stripper was started. Then the acid water workup was ready for restarting of the production plant. The time taken to start the acid water stripper including the analysis of the acidic wastewater for organics by means of gas chromatography was 1 hour.

In parallel to the washes and the distillation, the alkaline wastewater workup was started by supplying thermal pressure decomposition which had been put in circulation mode with 0.6 t/h of 110 bar steam, in order to bring the circulation water from 85° C. to 285° C. 2 hours prior to the discharge of the alkaline wastewater, the stripper was supplied with 0.5 t/h of 6 bar steam and the inlet and outlet of the alkaline wastewater to and from the stripper were started by starting the wastewater pumps. The time taken was 8 hours.

One and a half hours before the washes and distillation were ready for restarting of the production plant and after the acid water workup was running in circulation mode, the sulfuric acid circulation pump was started and the sulfuric acid was run in circulation through the nitrator, phase separation apparatus, flash evaporator and sulfuric acid reservoir tank. In the flash evaporator, the vacuum was started and then 2.4 t/h of 6 bar steam were applied, which heated the circulating sulfuric acid to starting temperature. This operation took 1 hour until the circulating sulfuric acid cooled down to 93° C. had been heated up to 100° C.

After 4.5 hours, the washes and the distillation were ready for operation and the production plant was started by starting the benzene and nitric acid pumps with 50% of the nameplate capacity, which corresponded to a production output of 25 t/h of nitrobenzene. After 1 minute, the reaction product arrived in the phase separation apparatus and the acid water stripper was set to discharge of the acidic wastewater and the bottoms column of the distillation was set to product discharge of the nitrobenzene end product. The running of the production plant up to nameplate load, which is automated in a modern production plant, takes another 1 hour.

Assessment of the Energy and Auxiliaries Required and Time Taken for the Running Down and Starting Up of the Plant Including the Cleaning Measure:

The total time taken for the measure was 15 hours. This applies if sufficient personnel is available and no technical difficulties occur. The time taken for the cleaning itself was 8 hours. For the shutdown, 2.5 hours were required. The startup took 4.5 hours.

Thus, a total of 775 tonnes of nitrobenzene production was lost. The steam consumption was 4.4 tonnes of 6 bar steam, 8 tonnes of 16 bar steam and 4.8 tonnes of 110 bar steam. In the running down of the plant and during the measure, no steam was consumed. The consumption of nitrogen for the running down was 550 m$^3$ (STP) and for the restart of the plant was 100 m$^3$ (STP). The consumption of condensate was 15.5 m$^3$ (2 m$^3$ for the purging of the heat exchanger and 13.5 m$^3$ for the startup of the neutral wash). The consumption of power totaled 6130 kW. For the running down of the plant, 1100 kW were required for the TDZ, 180 kW for the nitration and 445 kW for the washes. For the startup of the plant, 4005 kW were required for the washes and 400 kW for the circulating sulfuric acid pumps. During the cleaning measure, no power was consumed.

Example 2 (Inventive): Brief Shutdown of the Production Plant with Circulation Mode in the Plant Sections Unaffected by the Cleaning Measure, Cleaning Measure and Restarting of the Plant The brief shutdown of the plant served for cleaning operations in the nitration region. For this purpose, the nitration region was run down completely and the other plant sections such as the washes, the distillation, and the acidic and alkaline wastewater workup were put in circulation mode. The energy supplies during the cleaning operations were switched off only in the nitration region (the vacuum remained on standby). After the cleaning operations, the plant was started up again, for which it was necessary to completely inertize, fill and heat up only the nitration region.

Procedure for the Complete Stoppage of the Nitration and Adjustment of the Remaining Plant Sections to Circulation Mode:

Firstly, the acid water workup was put in circulation mode by switching the discharge of the acidic wastewater into the wastewater channel back into the acid water reservoir tank by means of the bottoms pump of the stripper, which requires 10 kW/h. The steam to the acid water stripper was throttled from 1.2 t/h to 0.7 t/h of 6 bar steam and the feed of acid water from the acid water reservoir tank by means of the acid water pump, which requires 10 kW/h, into the acid water stripper was reduced from 20 m$^3$ to 13 m$^3$. The changeover of the acid water workup to circulation mode took place within 33 seconds by means of automation.

Next, the alkaline wastewater workup was put in circulation mode by switching the discharge of the alkaline wastewater of the thermal pressure decomposition (TDZ) into the wastewater channel back into the alkaline wastewater reservoir by means of the high-pressure pump of the TDZ, which requires 55 kW/h. The steam to the pressure decomposition was throttled from 0.32 t/h to 0.20 t/h of 110 bar steam and the feed of alkaline wastewater from the alkaline wastewater reservoir into the TDZ was reduced from 4.0 m$^3$/h to 2.5 m$^3$/h. The changeover of the TDZ to circulation mode took place within 5 minutes by means of automation, because the reduction of the feed to the TDZ was effected manually.

At the same time, the stripper of the alkaline wastewater was put in circulation mode by interrupting the discharge of the alkaline wastewater into the TDZ and switching the alkaline wastewater back to the wastewater tank by means of the bottoms pump of the stripper, which requires 10 kW/h. The steam to the stripper for the alkaline wastewater was throttled from 0.4 t/h to 0.25 t/h of 6 bar steam, and the feed of alkaline wastewater from the wastewater tank into the stripper for the alkaline wastewater was reduced from 4 m$^3$ to 2.5 m$^3$ by means of the injection pump for the alkaline wastewater, which requires 10 kW/h. The changeover of the stripper for the alkaline wastewater to circulation mode took place within 27 seconds by means of automation.

Next, the washes and the distillation were put in circulation mode by switching the discharge of the nitrobenzene end product from the nitrobenzene column to the nitrobenzene storage tank over to the crude nitrobenzene tank by means of the bottoms pump of the column, which requires 24 kW/h. At the same time, the benzene-containing organic phase of the vapor phase separation apparatus was guided by means of natural efflux to the crude nitrobenzene tank. The aqueous phase of the vapor phase separation apparatus was disposed of via the acidic wash and the acidic wastewater workup. The vacuum system of the nitrobenzene column remained in operation. The circulation mode was established by running the contents of the crude nitrobenzene tank by means of delivery pumps through all the washes back to the nitrobenzene column. The crude nitro tank, the acidic wash, the alkaline wash and the 3 neutral washes each have a delivery pump, each of which requires 24 kW/h. The feed of crude nitrobenzene into the washes or distillation was reduced from 42 t/h to 27 t/h. The steam to the nitrobenzene column was throttled from 2.5 t/h to 1.6 t/h of 16 bar steam. The wash water for the neutral wash was reduced from 6.3 $m^3/h$ to 4.0 $m^3/h$. The changeover of the washes and the distillation to circulation mode took place within 5 minutes by means of automation.

Lastly, the nitration was shut down by switching off the metering pumps for the input streams of benzene and nitric acid. The vapor from the flash evaporator was stopped 5 minutes after the benzene and nitric acid raw materials. The circulation of sulfuric acid continued for 1 hour until all organics were discharged from the nitration circuit consisting of nitrators, phase separation apparatus, flash evaporator and circulating sulfuric acid reservoir tank. Then the circulation of sulfuric acid at 100° C. was interrupted by switching off the circulation pump. The nitrators, the phase separation apparatus and the flash evaporator were left under standing sulfuric acid. The remaining circulating sulfuric acid was in the sulfuric acid reservoir tank. Simultaneously with the circulation pump, the vacuum pump to the flash evaporator was shut down and the vacuum was broken with 350 $m^3$ (STP) of nitrogen. The nitration circuit was then at rest. The time taken for the shutdown was 2 hours.

The preparation (establishing circulation mode of washing, distillation, alkaline and acidic wastewater and the shutdown of the nitration) for the cleaning measure took a total of 2 hours and 11 minutes without purging and emptying of the apparatuses, pumps and pipelines.

Procedure for the Cleaning Measure:
The cleaning measure was conducted as described in example 1.

Procedure for the Restarting of the Plant:
The vacuum pump for the flash evaporator was put in operation beforehand. The phase separation apparatus and the cleaned benzene preheater were inertized with 100 $m^3$ (STP) of nitrogen. The startup of the plant was started with the starting of the nitration, by starting the sulfuric acid circulation pump and running the sulfuric acid in circulation through the nitrator, phase separation apparatus, flash evaporator and sulfuric acid reservoir tank. In the flash evaporator, the vacuum had already been started, and then 2.4 t/h of 6 bar steam were applied, which heated the circulating sulfuric acid to starting temperature. This operation took 1 hour until the circulating sulfuric acid cooled down to 93° C. had been heated up to 100° C. Then the nitration was started by starting the benzene and nitric acid pumps at 50% of the nameplate capacity, which corresponded to a production output of 25 t/h of nitrobenzene. After 1 minute, the reaction product arrived in the phase separation apparatus, the acid water stripper was set to discharge of the acidic wastewater and the bottoms column of the distillation was set to product discharge of the nitrobenzene end product. At the same time, the stripper for the alkaline wastewater workup was switched to discharge to the TDZ, and the TDZ was switched from circulation mode to discharge into the wastewater channel. The running of the production plant up to nameplate load, which is automated in a modern production plant, took another 1 hour.

Assessment of the Energy Required and Time Taken for the Running Down and Starting Up of the Plant from Circulation Mode, Including the Cleaning Measure:

The total time taken for the measure was 11 hours and 12 minutes. This applies particularly if sufficient personnel is available and no technical difficulties occur. The time taken for the cleaning itself was 8 hours. The running down into circulation mode took 2 hours and 11 minutes. The startup from circulation mode took 1 hour and 1 minute.

In this way, a total of 585 tonnes of nitrobenzene production was lost. The steam consumption was 12 tonnes of 6 bar steam, 13 tonnes of 16 bar steam and 1.6 tonnes of 110 bar steam for the circulation mode. In the running down of the plant into circulation mode, no steam was consumed. The consumption of nitrogen for the running down into circulation mode was 350 $m^3$ (STP) and for the restart of the plant from circulation mode was 100 $m^3$ (STP). The consumption of condensate for the measure was 47 $m^3$ (2 $m^3$ for the purging of the heat exchanger and 45 $m^3$ for the running down and startup and circulation mode of the washes). The consumption of power totaled 8525 kW. The running down of the plant consumed 1943 kW, the circulation mode during the cleaning measure consumed 5680 kW for the circulation mode and the startup of the plant consumed 905 kW of power.

Conclusion for the Complete Stoppage (Comparative Example 1) Versus Circulation Mode (Example 2) for the Cleaning Measure:

As a conclusion for the complete stoppage (comparative example 1) versus circulation mode (example 2), it can be stated that the extra demand for power and condensate is more than compensated for by the lower consumption of nitrogen, but particularly by the higher availability of the plant, which is manifested by a higher production output. The steam consumption is about the same. The time saved for the cleaning measure is 3 hours and 48 minutes, which corresponds to an improved production output of 190 tonnes of nitrobenzene.

Example 3 (Comparative Example): Brief Shutdown of the Production Plant with Complete Stoppage of the Plant, Repair Measure and Restarting of the Plant Brief Shutdown of the Plant for a Repair Measure in the Washing Operation For this purpose, the plant was run down completely, i.e. nitration, washes and distillation. The energy supplies were switched off during the repair measure. After the repair, the plant was started up again, for which it was necessary to inertize, fill and heat the entire plant.

Procedure for the Complete Stoppage of the Plant:
The plant was shut down as described in example 1. The complete stoppage again took two hours without purging and emptying of the apparatuses, pumps and pipelines, neglecting the running-down of the TDZ.

Procedure for the Repair Measure:
Sealing of leaky pipeline in the neutral wash: For this purpose, the pipeline affected in the downstream washing apparatus was blown clear with 10 $m^3$ of nitrogen. Then the pipeline was purged with 2 $m^3$ of condensate and emptied. Subsequently, the failed seal in the pipeline was replaced.

The repair measure took a total of 1.5 hours. In modern automated production plants, the number of personnel required for the preparation for the repair, namely the purging of the pipeline, plays an important role. In this case, one additional production worker is required. Workmen for disassembly and assembly of the pipeline in order to replace the failed seal are likewise required.

Procedure for the Restarting of the Plant:

The vacuum pumps in the entire production plant were put in operation beforehand.

Subsequently, the plant was restarted as described in example 1. The plant had been started up again after 4.5 hours and could be run up to nameplate load.

Assessment of the Energy Required and Time Taken for the Running Down and Starting Up of the Plant, Including the Cleaning Measure:

The total time taken for the measure was 8.5 hours, since sufficient personnel were available and no technical difficulties occurred. The time taken for the repair itself was 1.5 hours. For the shutdown, 2.5 hours were required. The startup took 4.5 hours. Thus, a total of 450 tonnes of nitrobenzene production was lost. The steam consumption was 3.4 tonnes of 6 bar steam and 8 tonnes of 16 bar steam and 4.8 tonnes of 110 bar steam. In the running down of the plant, no steam was consumed. A total of 610 m$^3$ (STP) of nitrogen were required, of which 550 m$^3$ (STP) was for the running-down and 50 m$^3$ (STP) for the restarting of the plant, and a further 10 m$^3$ (STP) for the repair measure.

The consumption of condensate was 15.5 m$^3$ (2 m$^3$ for the purging of the pipeline and 13.5 m$^3$ for the startup of the neutral wash). The consumption of power totalled 5470 kW. For the running down of the plant, 440 kW were required for the TDZ, 180 kW for the nitration and 445 kW for the washes. For the startup of the plant, 4005 kW were required for the washes and 400 kW for the circulating sulfuric acid pumps. During the repair measure, no power was consumed.

Example 4 (Inventive): Brief Shutdown of the Production Plant with Circulation Mode in the Plant Sections Unaffected by the Repair Measure, Repair Measure and Restarting of the Plant Brief shutdown of the plant for repair operations in the nitrobenzene wash: For this purpose, the washes and distillation were run down completely. The other plant sections such as the nitration and the acidic and alkaline wastewater workup were put in circulation mode. The energy supplies during the repair operations were switched off only in the wash and the distillation (vacuum remained on standby). After the repair, the plant was restarted.

Procedure for the Complete Stoppage of the Washes and Distillation and Adjustment of the Remaining Plant Sections to Circulation Mode:

Firstly, the acid water workup was put in circulation mode by switching the discharge of the acidic wastewater into the wastewater channel back into the acid water reservoir tank by means of the bottoms pump of the stripper, which requires 10 kW/h. The steam to the acid water stripper was throttled from 1.2 t/h to 0.7 t/h of 6 bar steam and the feed of acid water from the acid water reservoir tank by means of the acid water pump, which requires 10 kW/h, into the acid water stripper was reduced from 20 m$^3$ to 13 m$^3$. The changeover of the acid water workup to circulation mode took place within 29 seconds by means of automation.

Next, the alkaline wastewater workup was put in circulation mode by switching the discharge of the alkaline wastewater of the thermal pressure decomposition (TDZ) into the wastewater channel back into the alkaline wastewater reservoir by means of the high-pressure pump of the TDZ, which requires 55 kW/h. The steam to the pressure decomposition was throttled from 0.32 t/h to 0.20 t/h of 110 bar steam and the feed of alkaline wastewater from the alkaline wastewater reservoir into the TDZ was reduced from 4.0 m$^3$/h to 2.5 m$^3$/h. The changeover of the TDZ to circulation mode took place within 5 minutes by means of automation, because the reduction of the feed to the TDZ was effected manually.

At the same time, the stripper of the alkaline wastewater was put in circulation mode by interrupting the discharge of the alkaline wastewater into the TDZ and switching the alkaline wastewater back to the wastewater tank by means of the bottoms pump of the stripper, which requires 10 kW/h. The steam to the stripper for the alkaline wastewater was throttled from 0.4 t/h to 0.25 t/h of 6 bar steam, and the feed of alkaline wastewater from the wastewater tank into the stripper for the alkaline wastewater was reduced from 4 m$^3$ to 2.5 m$^3$ by means of the injection pump for the alkaline wastewater, which requires 10 kW/h. The changeover of the stripper for the alkaline wastewater to circulation mode took place within 31 seconds by means of automation.

Next, the feedstocks to the nitration were stopped. The metering pumps for the input streams of benzene and nitric acid were switched off. The circulating sulfuric acid continued to circulate at 100° C. through the nitrators, the phase separation apparatus, flash evaporator and circulating sulfuric acid reservoir tank. The flash evaporator required 0.3 t/h of 6 bar steam. The time taken was 1 minute.

Lastly, the washes were shut down by interrupting the crude nitrobenzene feed from the crude nitrobenzene tank to the acidic wash. The crude nitrobenzene pathway through the acidic, alkaline and neutral wash was stopped by stopping the delivery pumps for the crude nitrobenzene upstream of the respective washes. The washes were at 48° C. and remained filled with crude nitrobenzene. At the same time, the acidic, alkaline and neutral wash water pathway was stopped by switching off the respective pumps. The time taken was 5 minutes.

Then the distillation was shut down by interrupting the feed of crude nitrobenzene and taking away the steam to the distillation column. Immediately thereafter, the product discharge was interrupted by switching off the bottoms pump and the return stream at the top of the column was stopped by stopping the benzene pump. The vacuum pump continued to run. The time taken was 5 minutes.

The preparation (establishment of circulation mode in the nitration and the alkaline and acidic wastewater workup and the shutdown of the washes and distillation) for the repair measure took a total of 11 minutes without purging and emptying of the apparatuses, pumps and pipelines.

Procedure for the Repair Measure:

The repair measure was conducted as described in example 3. The time taken was again 1.5 hours. The steam consumption during circulation mode was 1.6 tonnes of 6 bar steam and 0.4 tonne of 110 bar steam. 400 kW of power were required for the operation of the vacuum pump and sulfuric acid circulation pump during circulation mode.

Procedure for the Restarting of the Plant:

Firstly, the washes were started by starting the crude nitrobenzene pump to put the crude nitrobenzene supply from the crude nitrobenzene tank to the acidic wash into operation. Thereafter, the acidic, alkaline and neutral wash water pathway was started by switching on the respective pumps. Then the crude nitrobenzene pathway through the acidic, alkaline and neutral wash was started by switching on the delivery pumps for the crude nitrobenzene upstream of the respective washes. The washing apparatuses that were filled with crude nitrobenzene and wash water were at 45° C. and were gradually warmed back up to 48° C. after the production plant had been started.

Once the last stage of the neutral wash had been put in operation by feeding in 3 t/h of condensate, the distillation was started by running crude nitrobenzene at 45° C. from the last neutral wash to the distillation column. Thereafter, the bottoms pump of the column was started and crude nitrobenzene was run to the crude nitrobenzene tank. Then the distillation column was supplied with 2 t/h of 16 bar steam and heated up to 170° C. At 50° C. at the top of the column, the reflux was put in operation by starting the benzene pump. The washes and the distillation were ready for restarting of the production plant after 1 hour.

Then the nitration was started by starting the benzene and nitric acid pumps at 50% of the nameplate capacity, which corresponded to a production output of 25 t/h of nitrobenzene. After 1 minute, the reaction product arrived in the phase separation apparatus, the acid water stripper was set to discharge of the acidic wastewater and the bottoms column of the distillation was set to product discharge of the nitrobenzene end product. At the same time, the stripper for the alkaline wastewater workup was switched to discharge to the TDZ, and the TDZ was switched from circulation mode to discharge into the wastewater channel. The running-up of the production plant to nameplate load took another 1 hour.

Assessment of the Energy Required and Time Taken for the Running Down and Starting Up of the Plant from Circulation Mode, Including the Repair Measure:

The total time taken for the measure was 3 hours and 41 minutes. The time taken for the repair itself was 1.5 hours. The running down into circulation mode took 11 minutes. The startup from circulation mode took 1 hour and 1 minute.

Thus, a total of 165 tonnes of nitrobenzene production was lost. The steam consumption was 1.6 tonnes of 6 bar steam, 2 tonnes of 16 bar steam and 0.8 tonne of 110 bar steam. In the running down of the plant into circulation mode, no steam was consumed. 10 m$^3$ (STP) of nitrogen were required for the repair measure and 50 m$^3$ (STP) of nitrogen for the restarting of the plant. The consumption of condensate was 7 m$^3$ (2 m$^3$ for the purging of the pipeline and 5 m$^3$ for the running-down and startup of the neutral wash). The consumption of power totaled 1593 kW. The running-down of the plant consumed 178 kW for the running-down of the nitration into circulation mode, 510 kW for the circulation mode during the cleaning measure and 905 kW of power for the startup of the plant.

Conclusion for the Complete Stoppage (Comparative Example 3) Versus Circulation Mode (Example 4) for the Repair Measure:

As a conclusion for the complete stoppage (comparative example 3) versus circulation mode (example 4), it can be stated that smaller amounts of steam, power, nitrogen and condensate were consumed in circulation mode and, on top of that, the availability of the plant, which is manifested by a higher production output, was distinctly better. The time saved for the repair measure was 5 hours and 48 minutes, which corresponds to an improved production output of 290 tonnes of nitrobenzene.

The invention claimed is:

1. A process for preparing nitrobenzene, comprising
   (I) nitrating benzene with nitric acid in sulfuric acid to form nitrobenzene in a reactor, with introduction of a mass flow of benzene ($m_1$), a mass flow of nitric acid ($m_2$), and a mass flow of sulfuric acid ($m_3$), into the reactor, thereby obtaining a reaction mixture comprising an organic nitrobenzene-containing phase and an aqueous sulfuric acid-containing phase;
   (II) separating the organic nitrobenzene-containing phase and the aqueous sulfuric acid-containing phases of the reaction mixture from (I) in a phase separation apparatus;

and optionally (III) to (VII):
   (III) concentrating the aqueous sulfuric acid-containing phase separated in (II) by evaporating water in an evaporation apparatus to give an aqueous sulfuric acid-containing phase having elevated sulfuric acid concentration, with recycling of the concentrated sulfuric acid-containing aqueous phase via a sulfuric acid tank into (I) and use thereof as a constituent of the mass flow $m_3$;
   (IV) washing the organic nitrobenzene-containing phase obtained in (II) in at least two stages and separating off an aqueous phase after each stage, using a wash vessel having a phase separation unit or a wash vessel and a separate phase separation apparatus in each stage,
   (V) distilling the organic nitrobenzene-containing phase obtained in the last stage of (IV) in a distillation apparatus, and
   (VI) working up the aqueous phase from the first wash stage of (IV), comprising collecting the aqueous phase in a wastewater collection vessel and cleaning said aqueous phase in an apparatus for distillation or stripping,
   and
   (VII) working up the aqueous phase from the second wash stage of the at least two wash stages of (IV), comprising collecting the aqueous phase in a wastewater collection vessel and cleaning said aqueous phase in an apparatus for distillation or stripping, where the apparatus for distillation or stripping may be connected up- and/or downstream of an apparatus for thermal pressure decomposition,
   wherein
   the process is interrupted, the interruption comprising the steps of shutting down one or more, but not all, plant sections from (I) to (VII), reducing the mass flow $m_1$ and the mass flow $m_2$ to zero and, in at least one of the plant sections that has not been shut down, using an output stream of said at least one plant section that has not been shut down as an input stream for the respective plant section or an upstream plant section, thereby operating said at least one plant section that has not been shut down in circulation mode.

2. The process as claimed in claim 1, additionally comprising (III) to (VII).

3. The process as claimed in claim 2, wherein (IV) comprises
   (IVa) washing the organic nitrobenzene-containing phase obtained in (II) in at least one wash stage, and separating phases into a first aqueous phase and a first organic nitrobenzene-containing phase,
   (IVb) washing the first organic nitrobenzene-containing phase obtained in (IVa) in at least one alkaline wash with an aqueous solution of a base selected from the group consisting of sodium hydroxide, sodium carbonate and sodium hydrogencarbonate, and separating phases into a second aqueous phase and a second organic nitrobenzene-containing phase,
   and (IVc) washing the second organic nitrobenzene-containing phase obtained in (IVb) in at least one neutral wash with water, and separating phases into a third aqueous phase and a third organic nitrobenzene-containing phase.

4. The process as claimed in claim 1, wherein an output stream in every plant section that has not been shut down is used again as an input stream for the corresponding plant section or an upstream plant section.

5. The process as claimed in claim 2, wherein an output stream from the plant section from (V) is used as an input stream for the plant section from (IV).

6. The process of claim 1, additionally comprising
(1) at least one of:
 (a) conducting an inspection, repair, cleaning or maintenance measure in the one or more plant sections that have been shut down,
 and
 (b) compensating for a lack of feedstocks or auxiliaries, during the interruption of the process;
and
(2) restarting the process again after completion of said inspection, repair, cleaning or maintenance measure, or after the lack of feedstocks or auxiliaries has been overcome.

* * * * *